US008367054B2

(12) United States Patent
Bandyopadhyay et al.

(10) Patent No.: US 8,367,054 B2
(45) Date of Patent: Feb. 5, 2013

(54) FORMULATIONS OF PEG-INTERFERON ALPHA CONJUGATES

(75) Inventors: Sanjay Bandyopadhyay, Ahmedabad (IN); Venkatesan Natarajan, Ahmedabad (IN); Sanjeev Kumar Mendiratta, Ahmedabad (IN); Pankaj Ramanbhai Patel, Ahmedabad (IN)

(73) Assignee: Cadila Healthcare Limited, Ahmedabad (IN)

( * ) Notice: Subject to any disclaimer, the term of this patent is extended or adjusted under 35 U.S.C. 154(b) by 434 days.

(21) Appl. No.: 12/515,975

(22) PCT Filed: Nov. 16, 2007

(86) PCT No.: PCT/IN2007/000549
§ 371 (c)(1),
(2), (4) Date: Aug. 25, 2009

(87) PCT Pub. No.: WO2008/062481
PCT Pub. Date: May 29, 2008

(65) Prior Publication Data
US 2010/0074865 A1     Mar. 25, 2010

(30) Foreign Application Priority Data

Nov. 24, 2006   (IN) .................. 1936/MUM/2006

(51) Int. Cl.
*A61K 38/21*   (2006.01)
*A61K 38/00*   (2006.01)
*C07K 14/56*   (2006.01)

(52) U.S. Cl. .................. 424/85.7; 530/351; 514/1.1
(58) Field of Classification Search .......... None
See application file for complete search history.

(56) References Cited

U.S. PATENT DOCUMENTS

| | | | |
|---|---|---|---|
| 4,179,337 A | 12/1979 | Davis | |
| 4,496,537 A * | 1/1985 | Kwan | .......... 424/85.7 |
| 4,766,106 A | 8/1988 | Katre | |
| 4,917,888 A | 4/1990 | Katre | |
| 5,612,460 A | 3/1997 | Zalipsky | |
| 5,711,944 A | 1/1998 | Gilbert | |
| 5,951,974 A | 9/1999 | Gilbert | |
| 5,981,709 A | 11/1999 | Greenwald | |
| 6,180,096 B1 | 1/2001 | Kline | |

FOREIGN PATENT DOCUMENTS

| WO | 2004/076474 | 9/2004 |
|---|---|---|
| WO | 2006/020720 | 2/2006 |

OTHER PUBLICATIONS

International Search Report issued during international phase of counterpart PCT application PCT/IN2007/000549 (Nov. 12, 2008).*
Written Opinion issued during international phase of counterpart PCT application PCT/IN2007/000549 (May 24, 2009).*
International Preliminary Report on Patentability issued during international phase of counterpart PCT application PCT/IN2007/000549 (May 24, 2009).*
McHutchinson et al., "Interferon alfa-2b alone or in combination with ribavirin as intial treatment for chronic hepatitis C":Engl. J. Med. 339(21):1485-1492 (1998).
Glue et al., "Pegylated interferon-a2b: Pharmacokinetics, pharmacodynamics, safety, and preliminary efficacy data" Clin. Pharmacol. Ther. 68:556-567 (2000).
Monkarsh SP. et al., "Positional isomers of monopegylated interferon a-2a: Isolation, characterization, and biological activity": Analytical Biochemistry 247(2):434-40 (May 1, 1997).
Thanou et al., "Polymer-protein and polymer-drug conjugates in cancer therapy": Curr. Opin. Invest. Drugs 4 (6):701-709 (Jun. 2003).
Costantino, Henry R. and Pikal, Michael J., "Excipients for Use in Lyophilized Pharmaceutical Peptide, Protein, and other Bioproducts", Lyophilization of Biopharmaceuticals, V. 2, p. 139-228 (2004) American Association of Pharmaceutical Scientists, USA.
Banga, Ajay K., "Formulation of Therapeutic Peptide and Proteins", Therapeutic Peptides and Proteins: Formulation, Processing, and Delivery Systems, p. 81-163 (1995) Technomic Publishing Company, Inc., USA.
Submission to European Patent Office published Jan. 16, 2004 in European Application No. 99913822, granted as EP 1066059, and counterpart to US Patent No. 6,180,096 (Kline).

* cited by examiner

*Primary Examiner* — Robert Landsman
*Assistant Examiner* — Bruce D Hissong
(74) *Attorney, Agent, or Firm* — Iphorgan Ltd.

(57) ABSTRACT

Lyophilized and stabilized formulations of PEG-Interferon alpha conjugates and the process for their preparation that reduces lyophilization cycle time and are more cost competitive.

19 Claims, No Drawings

FORMULATIONS OF PEG-INTERFERON ALPHA CONJUGATES

CROSS-REFERENCE TO RELATED APPLICATIONS

This is a Sect. 371 National Stage of PCT International Application No. PCT/IN2007/000549, filed on 16 Nov. 2007, claiming priority of Indian Patent Application No. 1936/MUM/2006 filed on 24 Nov. 2006, the contents of both applications hereby being incorporated by reference.

FIELD OF INVENTION

The present invention relates to novel lyophilized and stabilized formulations of PEG-Interferon alpha conjugates and processes for their preparation.

BACKGROUND OF THE INVENTION

The major disadvantage with the therapeutic use of most biologicals is that they are administered through parenteral route e.g., intravenously (i.v.), subcutaneously (s.c.), intramuscularly (i.m.) etc., which means that delivery to the patient is associated with pain and discomfort. Further, because of their usually very short half-lives, biologicals require frequent administrations into the patient in order to maintain therapeutic blood levels of the drug. Many types of injections that cannot be self-administered, require frequent trips to the clinic, further adding to the discomfort of the patient. Multiple examples of such biological drugs that require frequent administration exist. Interferon alpha-2a (Roferon, Roche) and interferon alpha-2b (Intron A, Schering AG), the two recombinant forms of human interferon alpha, used in the treatment of chronic hepatitis B and C have a serum half-life of less than 12 h (McHutchison, et al., Engl. J. Med. 1998, 339, 1485-1492; Glue, et al., Clin. Pharmacol. Ther. 2000, 68, 556-567) and therefore requiring 3 times a week administration. Repeated injections with interferon beta-1b (Betaseron) are also required to treat the patients of multiple sclerosis (MS). The recommended dosing is by subcutaneous route given every other day. Another example of a drug where repeated injections are required is filgrastim (granulocyte colony stimulating factor, or G-CSF), where the injection is given everyday for the duration of treatment two weeks.

One very successful and well accepted method of overcoming the above drawbacks of frequent high dose injections to maintain threshold levels of the drug in the body is to increase the in-vivo half-life of the therapeutic protein by conjugating it with a polymer, preferably polyethylene glycol (PEG). PEG molecules with their long chains not only create a protective shield around the pegylated drug molecule in aqueous solution, thereby, reducing the immunogenicity of protein drugs while also protecting them from the action of proteases, but they further help increase circulation half-life of the drug by increasing its hydrodynamic volume which reduces its loss from the filtration mechanisms of the kidney glomeruli network. After their separation from the protein molecule, the PEG moieties are cleared without any structural changes and their clearance is proportional to their molecular weight. Conjugation of proteins to PEG has been reported since 1970s. Usually PEG moieties are attached to the protein by first activating the PEG moiety and then reacting it with the side chain of lysine residue and/or the N-terminal amino group on the protein. The most frequently used PEG is monofunctional PEG because this moiety resists cross-linking and aggregation. One such example has been disclosed by Davis et al. in U.S. Pat. No. 4,179,337. PEG_protein conjugates were formed by reacting a biologically active material with a molar excess concentration of a highly activated polymer having a terminal linking group without regard to where the polymer would attach to the protein, and leading to a physiologically active non-immunogenic water soluble polypeptide composition. Pegylation of interferons has been reported in U.S. Pat. Nos. 4,766,106 and 4,917,888 which describe inter alia beta interferon conjugated with activated polymers including mPEG-2,4,6-trichloro-S-triazine, mPEG-N-succinimidyl glutarate or mPEG-N-succinimidyl succinate. One such disclosure in U.S. Pat. No. 5,951,974 describes the conjugation of interferon to a substantially non-antigenic polymer at a histidine site. Another such disclosure in U.S. Pat. No. 5,981,709 describes the alpha interferon-polymer conjugate with relatively long circulating half-life in-vivo.

Some commercially available pegylated therapeutic proteins include, ADAGEN (pegylated bovine adenosine deaminase), which is used to treat X-linked severe combined immunogenicity syndrome; PEGASYS (pegylated alpha-interferon 2a), which is used in the treatment of hepatitis C; PEG-Intron (pegylated alpha-interferon 2b) for chronic hepatitis C; Oncaspar (pegylated L-asparaginase) for the treatment of acute lymphoblastic leukemia in patients who are hypersensitive to the native unmodified form of L-asparaginase; and, Neulasta (pegylated recombinant methionyl human granulocyte colony stimulating factor) for cancer chemotherapy induced neutropenia.

Hepatits C virus (HCV) is one of the major causes of liver disease in the world. Nearly 200 million people are affected world wide. Interferon in combination with ribavirin has been shown to be effective in decreasing the viral load of patients with chronic hepatitis C, however it needs to be given three times a week. PEG-interferon alpha 2b is a covalent conjugate of recombinant interferon alpha 2b with monomethoxy PEG in a 1:1 molar ratio (Glue P et al., Clin Pharmacol Ther. 2000; 68; 556-567). The mean absorption half-life of PEG-interferon alpha 2b is 5 fold greater than non-pegylated interferon alpha-2b. The mean elimination half-life is 40 hours in patients with hepatitis C infection. Another product is PEG-interferon alpha 2a, which has a 40 kDa branched chain molecule with each PEG branch with an average molecular weight of 20 kDa. The two monomethoxy PEG chains are joined via hydrolytically stable urethane bonds to a lysine linker molecule, one at the lysine alpha-amino group and another at the lysine ε-amino group. The mean absorption half-life of PEG-interferon alpha 2a is 10 fold greater than non-pegylated interferon alpha-2a. The mean elimination half-life is about 60 hours in patients with hepatitis C infection. Both these improved products need to be administered at once a week regimen only.

While, some protein-polymer conjugates are stable in the liquid form, others are not. For example, unlike the case of PEG-interferon alpha 2a where pegylation leads to a stable urethane bond, which is primarily stable in aqueous media, the PEG-interferon alpha 2b product, which contains PEG primarily linked to a histidine (His 34) residue, is highly unstable in the liquid form. With such protein-polymer conjugates, one has to use techniques such as lyophilization/freeze-drying—a process whereby water is sublimed from a composition after it is frozen—which can provide a stable form to the biological over a desired period of time. Thus, to make a stable formulation of PEG-interferon alpha 2b, one needs to carefully lyophilize the formulation with suitable cryoprotectant(s) or lyoprotectant(s), and stabilizers, that stabilize the pegylated interferon alpha conjugates to prevent depegylation during and after lyophilization—a phenomenon commonly associated with the PEG-interferon alpha 2b product. Further, besides the cryoprotectant and stabilizers the lyophilized formulation also contains bulking agents to increase the amount of the solid material in the vial.

One specific way in which the problem of instability of urethane linkage at His 34 residue has been resolved in the case of PEG-interferon alpha 2b, is by utilizing a formulation that has been disclosed in U.S. Pat. No. 6,180,096, where in the PEG-IFN alpha 2b conjugates are lyophilized in the presence of buffer, cryoprotectants, a stabilizer and a solvent of which one such formulation contains a disaccharide sucrose, as a cryoprotectant, along with, monobasic sodium phosphate dihydrate and dibasic sodium phosphate anhydrous, as buffer, with polysorbate 80 as a stabilizer, and water as a solvent. While the above formulation is commercially successful in the treatment of Hepatitis C, it is nevertheless associated with several problems some of which are elaborated in another patent application, WO2006/020720, by the same company, that sites longer lyophilization cycles leading to increased cost of manufacturing, and higher moisture content associated with the commercial formulation, as some of the reasons to discover and report novel formulation in WO2006/020720. In WO2006/020720, the inventors disclose another lyophilized formulation of PEG-IFN alpha 2b, wherein the cryoprotectant comprises of at least 60% trehalose, the buffering components comprise of monobasic sodium phosphate dihydrate and dibasic sodium phosphate anhydrous, and where the formulation further comprises of polysorbate 80 as a stabilizer and water as a solvent, and that is able to overcome the above described problems of the commercial formulation. The need for additional formulations for the protection of PEG-IFN alpha 2b conjugates cannot be better emphasized than the fact that the assignees of U.S. Pat. No. 6,180,096 (commercial formulation), and the applicants of WO2006/020720, are the same company, Schering Corporation, that is continuing to develop and disclose more lyophilized formulations for PEG-IFN alpha 2b.

The need for additional formulations of PEG-IFN alpha 2b to those in existence is with an aim not only to protect the PEG-interferon alpha conjugate during and after lyophilization, but also to have a long-term storage at room temperature when lyophilized in an appropriate container. The process of such formulations should be easy to handle and be more cost-effective than those used for the current formulation (sucrose based). The current commercial formulation of PEG-IFN alpha 2b, which is sucrose based (as described in U.S. Pat. No. 6,180,096), has a rather long lyophilization cycle of nearly 5 days. The formulation disclosed in the current invention uses a lyophilization cycle which is significantly shorter in time—approximately by 24-48 hours—which will help in significantly bringing down the cost of manufacturing this drug.

The present invention provides novel lyophilized and stabilized formulations of PEG-Interferon alpha conjugates and the process for their preparation.

EMBODIMENTS OF THE INVENTION

The main object of the invention is to provide novel lyophilized and stabilized formulations of PEG-Interferon alpha conjugates.

In an embodiment of the invention is provided a process for the preparation of novel formulations of PEG-Interferon alpha conjugates.

DESCRIPTION OF THE INVENTION

The present invention relates to novel lyophilized and stabilized formulations of PEG-Interferon alpha conjugates and process(es) for their preparation. The formulations involve formulating PEG-Interferon alpha conjugates with suitable buffer(s), suitable cryoprotectant(s), suitable stabilizer(s) and a solvent, optionally with other suitable excipients, which is subsequently lyophilized.

It will be appreciated that the present invention is not limited by the concentrations of the components in the novel formulations as is disclosed in the specification.

PEG-Interferon alpha conjugates according to the present invention are Interferon alpha molecules or their variants covalently linked to one or more PEG molecule/s. The PEG-Interferon alpha conjugates of the present invention may comprise of Interferon alpha-2a, Interferon alpha 2b or Interferon alpha-2c and their suitable variants. Preferably, the PEG-Interferon alpha conjugate is monopegylated Interferon alpha-2b.

Polymers, are molecules comprising covalently linked repeating chemical units. Often, the approximate molecular weight of the polymer is designated with a number following the name of the repeated chemical unit. For example, "$PEG_{12000}$" or "Polyethylene glycol (12000)" refers to a polymer of polyethylene glycol having an average molecular weight of approximately 12,000 daltons.

Conjugation of polymers to proteins may result in a single polymer molecule conjugated to a protein or multiple such conjugations to a single protein. The degree of conjugation is dependent upon the reaction conditions and desired result. In a preferred embodiment, the PEG-Interferon alpha conjugate in the formulations of the present invention comprises a single Interferon alpha-2b conjugated to a single PEG molecule. In a still preferred embodiment, the PEG-Interferon alpha conjugate in the formulations of the present invention comprises a single Interferon alpha-2b conjugated to a single $PEG_{12000}$. In a particularly preferred embodiment, the Interferon alpha-2b molecule is linked to the $PEG_{12000}$ molecule with a urethane bond. Several processes for preparing a Peg-IFN conjugates are known in the art and such processes and the products derived from such processes are considered to be encompassed within the scope of the present invention. Examples of such process(es) for producing this protein-polymer conjugate may be found in U.S. Pat. No. 5,612,460

(Zalipsky) and U.S. Pat. No. 5,711,944 (Gilbert et al). Without limiting the scope of the present invention, when such a protein-polymer conjugate is utilized in the formulation solutions of the present invention, the preferred concentration of PEG-Interferon alpha conjugate is 0.03 to 2.0 mg Interferon alpha per ml.

When a single interferon alpha molecule is linked to a single PEG-12000 molecule, the resulting conjugated PEG-interferon alpha conjugates may be in the form of a single or mixture of positional isomers. In an embodiment of the present invention, one such mixture of positional isomers could mean, the PEG-interferon alpha conjugate linked at a histidine residue of the interferon alpha molecule, while another PEG-interferon alpha conjugate is linked to another site of the interferon alpha molecule, for example the lysine residue.

To preserve the PEG-interferon alpha conjugate in the most stable and active form, lyophilization may be used. Lyophilization is a process of freeze-drying a composition wherein a frozen aqueous mixture is treated to remove water. Commonly, the process involves the sublimation of water from the aqueous solutions, usually under reduced pressure conditions. After lyophilization, the PEG-Interferon alpha conjugate(s) can be stored for extended periods of time.

PEG-Interferon alpha conjugates, however, are subject to damage during and after lyophilization (U.S. Pat. No. 6,180, 096). Hence, there is a need to suitably formulate the PEG-Interferon alpha conjugates so as to protect them from degradation during and after lyophilization. Moreover, it will also be useful if such formulations provide physical strength to the formulation.

The present invention protects PEG-Interferon alpha conjugates from damage by including them in formulations that prevent damage during and after lyophilization.

While the present invention is not limited to a particular formulation, the formulations that are anticipated here utilize a suitable buffer(s), suitable stabilizer(s), suitable cryoprotectant(s) and/or lyoprotectant(s), a bulking agent(s) and solvent(s), alone or in suitable combination, optionally with other suitable excipients, in addition to the PEG-Interferon alpha conjugate. Various possible combinations of the selected groups of buffers, stabilizers and cryoprotectants as described below, may be used to prepare the novel formulations of the present invention.

Buffers are suitable for maintaining pH of the formulation. The buffer system which may be used comprises of sodium phosphate, sodium succinate, potassium succinate, histidine chloride, sodium glycinate and the like, either alone or in suitable combination, which provides the desired pH range. The preferred pH range is between 4.5-7.1, preferably 6.5-7.1 and most preferably 6.8. The use of a buffer system of sodium succinate is preferred. The preferred molar concentration is in the range of 0.001 to 0.5 molar. Other buffer systems may also be used to maintain the desired pH range.

The term "cryoprotectants" generally includes agents which provide stability to the protein from freezing-induced stresses; however, the term also includes agents that provide stability, e.g., to bulk drug formulations during storage from non-freezing-induced stresses. Exemplary cryoprotectants include polyols, and include saccharides such as sucrose, lactose, trehalose, and mannitol, additionally including surfactants such as polysorbate, or polyethylene glycol, and the like. The term "cryoprotectant" includes agents that provide stability to the protein during water removal from the system during the drying process, presumably by maintaining the proper conformation of the protein through hydrogen bonding. Cryoprotectants can also have lyoprotectant effects; therefore, the terms "cryoprotectant" and "lyoprotectant" are used interchangeably herein.

A stabilizing agent is useful in the prevention of adsorption of the PEG-interferon alpha conjugates to glass and stainless steel surfaces of the process equipments used to make and store the formulation. Suitable stabilizing agents which may be used are sodium dodecyl sulphate (SDS), polysorbates (e.g., Polysorbate 20, 40 or 80, either alone, or in combination). Examples may be from the class of poly(oxy-1,2-ethanediyl) derivatives. One such preferred stabilizing agent is Polyoxyethylene 20 Sorbitan Mono-oleate, polysorbate 80 (Tween 80) at a preferred concentration of 0.01 to 1 mg/ml.

The present invention is not limited to a specific cryoprotectant or to any specific amount. The cryoprotectant may be used alone or in suitable combinations. In one embodiment, cryoprotectants are present in an amount of 0.05% to 90%, preferably 0.05-50% and most preferably in an amount of 0.15-20%, based on the total weight of the PEG-interferon alpha solution. In a specific example, when lactose is used alone as a cryoprotectant, the preferred concentration is 10-100 mg/ml.

Suitable solvent for the present formulation is water, preferably the solvent may be water for injection.

Other suitable excipients may be optionally added to the formulation. Such excipients include glycine at suitable concentration so as to further stabilize the formulation.

The novel formulations of PEG-Interferon alpha conjugates are prepared using suitable combinations of a buffer, stabilizer, cryoprotectant(s) &/or lyoprotectant(s) and a solvent, optionally with other excipients and suitably lyophilized and stored as a dry powder to be reconstituted before use.

The formulations prepared such, contain an effective amount of biologically active PEG-Interferon alpha conjugates, and are useful in treating several diseases such as Hepatitis B and C and cancer etc. They are preferably used as injectable aqueous solutions.

Following non-limiting examples illustrate the described pharmaceutical compositions of the present invention and the means of carrying out the invention to obtain a stable pharmaceutical dosage form of PEG-Interferon alpha conjugates. It will be appreciated that the Examples are illustrative and such other suitable modifications/additions etc. as are well within the scope of the persons skilled in the art are meant to be encompassed within the scope of the present invention.

EXAMPLES

Various formulations of PEG-interferon alpha-2b conjugated protein dissolved in sodium succinate buffer were prepared in the presence of lactose, under different experimental conditions, for lyophilization in glass vials in order to obtain a stable PEG-interferon alfa-2b conjugated protein in its composition. After lyophilization, samples were stored at 5° C. (±3° C.) and at different periods of time samples were reconstituted with water for analysis. The reconstituted samples were analyzed for visual clarity, protein content, antiviral activity, and level of free interferon. In antiviral assay, fresh, non-formulated, purified PEG-interferon alpha conjugate shows a specific activity in the range of $0.2 \times 10^8$ to $0.8 \times 10^8$ IU per milligram of interferon protein.

Example 1

PEG-interferon alpha conjugate prepared as per techniques known in the art was dissolved in an aqueous medium containing 10 mM sodium succinate buffer at pH 6.8, lactose (18 mg/mL), and polysorbate 80 (0.1 mg/mL), as summarized in Table 1.

TABLE 1

Components of the Formulation of PEG-Interferon Alpha Conjugate submitted to Lyophilization

| Components | Concentrations |
|---|---|
| $PEG_{12000}$-interferon alpha-2b | 0.178 mg/mL* |
| Sodium succinate, pH 6.8 | 10 mM |
| Lactose | 18 mg/mL |
| Polysorbate 80 | 0.1 mg/mL |
| Purified water | 0.7 mL |

*Based on protein weight

Lyophilization was carried out by placing the above specified solution in glass containers followed by loading the glass containers in to a lyophilizer at ambient pressure and a temperature between 10° C. to 30° C. Samples were frozen gradually in controlled manner at ambient pressure and at a temperature between −40° C. to −55° C. over a period of 3 to 12 hrs. Subsequently, frozen samples were subjected to primary drying in a step wise manner for at least 16 hrs at various temperatures ranging from −45° C. to 0° C., while maintaining a vacuum pressure from 500 mTorr to 50 mTorr. Following the primary drying cycles, secondary drying cycles were carried out for at least 6 hrs, under vacuum at a pressure between 20 to 30 mTorr. Upon completion of the lyophilization cycles, glass containers containing the lyophilized cakes were unloaded at ambient temperature and pressure.

After lyophilization, vials containing cakes with no defects (such as collapsed cakes or lidded cakes or shrunken cakes or melt-back cakes etc.) were collected and stored at 5 (±3)° C., until used for further analysis. Samples were reconstituted with water for analysis at different periods of time, as specified in Table 2. The reconstituted solutions were checked for visual clarity. Stability of PEG-interferon alpha conjugate in lyophilized formulation was assessed by comparing the protein content, antiviral activity, and level of free interferon (degree of depegylation) present in the solution before and after lyophilization (Table 2).

Example 2

PEG-interferon alpha conjugate was dissolved in an aqueous medium containing 10 mM sodium succinate buffer of pH 6.8, lactose (100 mg/mL), and polysorbate 80 (0.1 mg/mL), as summarized in Table 3.

TABLE 3

Components of the Formulation of PEG-Interferon Alpha Conjugate submitted to Lyophilization

| Components | Concentrations |
|---|---|
| $PEG_{12000}$-interferon alpha-2b | 0.178 mg/mL* |
| Sodium succinate, pH 6.8 | 10 mM |
| Lactose | 100 mg/mL |
| Polysorbate 80 | 0.1 mg/mL |
| Purified water | 0.7 mL |

*Based on protein weight

Lyophilization was carried out by placing the above specified solution in glass containers followed by loading the glass containers in to a lyophilizer at ambient pressure and a temperature between 10° C. to 30° C. Samples were frozen gradually in controlled manner at ambient pressure and at a temperature between −40° C. to −55° C. over a period of 3 to 12 hrs.

Subsequently, frozen samples were subjected to primary drying cycles at a temperature between −35° C. and −45° C. while maintaining a vacuum pressure from 500 mTorr to 50 mTorr. Following the primary drying cycles, second drying cycles were carried out for at least 6 hrs, under vacuum at a pressure between 20 to 30 mTorr. Upon completion of the lyophilization cycles, glass containers containing the lyophilized cakes were unloaded at ambient temperature and pressure.

After lyophilization, vials containing cakes with no defects were collected and stored at 5 (±3)° C., until used further for analysis. Samples were reconstituted with water for analysis at different periods of time, as specified in Table 4. The reconstituted solutions were checked for visual clarity. Stability of PEG-interferon alpha conjugate in lyophilized formulation was assessed by comparing the protein content, antiviral activity, and level of free interferon (degree of depegylation) present in the solution before and after lyophilization as shown in Table 4.

TABLE 2

Stability of Formulated PEG-Interferon Alpha Conjugate After Lyophilization

| Time (months) | Temp. (±3° C.) | Protein Content (μg/vial) | % Initial | Potency (IU/mg) | % Moisture | % Free IFN | Visual Clarity |
|---|---|---|---|---|---|---|---|
| Initial |   | 125.13 | 100.1 | $0.48 \times 10^8$ | 1.4 | 0.63 | CS |
| 3 | 5 | nd | Nd | $0.43 \times 10^8$ | 2.5 | 1.98 | CS |
| 6 |   | nd | Nd | $0.3 \times 10^8$ | nd | 2.34 | CS |
| 9 |   | 119.25 | 95.4 | $0.56 \times 10^8$ | nd | 2.54 | CS | nd—not determined;
CS—clear solution

TABLE 4

Stability of Formulated PEG-Interferon Alpha Conjugate After Lyophilization

| Time (months) | Temp. (±3° C.) | Protein Content | | Potency (IU/mg) | % Moisture | % Free IFN | Visual Clarity |
|---|---|---|---|---|---|---|---|
| | | (µg/vial) | % Initial | | | | |
| Initial | 5 | 123.2 | 98.6 | $0.58 \times 10^8$ | 0.25 | 0.84 | CS |
| 1 | | 119 | 95.4 | $0.35 \times 10^8$ | nd | 0.69 | CS |
| 3 | | 116 | 93 | $0.72 \times 10^8$ | nd | 0.79 | CS | nd—not determined;
CS—clear solution

Example 3

PEG-interferon alpha conjugate, at 0.2 mg/mL, was dissolved in an aqueous medium containing 10 mM sodium succinate buffer of pH 6.8, a mixture of cryoprotectants comprising lactose (57.1 mg/mL) and trehalose (31.4 mg/mL), and polysorbate 80 (0.1 mg/mL), as summarized in Table 5.

TABLE 5

Components of the Formulation of PEG-Interferon Alpha Conjugate submitted to Lyophilization

| Components | Concentrations |
|---|---|
| $PEG_{12000}$-interferon alpha-2b | 0.178 mg/mL* |
| Sodium succinate, pH 6.8 | 10 mM |
| Lactose | 57.1 mg/mL |
| Trehalose | 31.4 mg/mL |
| Polysorbate 80 | 0.1 mg/mL |
| Purified water | 0.7 mL |

*Based on protein weight

Lyophilization was carried out by placing the above specified solution in glass containers followed by loading the glass containers in to a lyophilizer at ambient pressure and a temperature between 10° C. to 30° C. Samples were frozen gradually in controlled manner at ambient pressure and at a temperature between −40° C. to −55° C. over a period of 3 to 12 hrs. Subsequently, frozen samples were subjected to primary drying cycles at a temperature between −35° C. and −45° C. while maintaining a vacuum pressure from 500 mTorr to 50 mTorr. Following the primary drying cycles, secondary drying cycles were carried out for at least 6 hrs, under vacuum at a pressure between 20 to 30 mTorr. Upon completion of the lyophilization cycles, glass containers containing the lyophilized cakes were unloaded at ambient temperature and pressure.

After lyophilization, vials containing cakes with no defects were collected and stored at 5 (±3)° C., until used further for analysis. Samples were reconstituted with water for analysis at different periods of time, as specified in Table 6. The reconstituted solutions were checked for visual clarity. Stability of PEG-interferon alpha conjugate in lyophilized formulation was assessed by comparing the protein content, antiviral activity, and level of free interferon (degree of depegylation) present in the solution before and after lyophilization as shown in Table 6.

TABLE 6

Stability of Formulated PEG-Interferon Alpha Conjugate After Lyophilization

| Time (months) | Temp. (±3° C.) | Protein Content | | Potency (IU/mg) | % Moisture | % Free IFN | Visual Clarity |
|---|---|---|---|---|---|---|---|
| | | (µg/vial) | % Initial | | | | |
| Initial | 5 | 123.2 | 98.56 | $0.72 \times 10^8$ | 0.23 | 0.91 | CS |
| 1 | | 115.18 | 92.2 | $0.5 \times 10^8$ | nd | 0.78 | CS |
| 3 | | 118.7 | 95 | $0.51 \times 10^8$ | nd | 0.92 | CS | nd—not determined;
CS—clear solution

Example 4

PEG-interferon alpha conjugate was dissolved in an aqueous medium containing 10 mM sodium succinate buffer of pH 6.8, lactose (40 mg/mL), trehalose (16 mg/mL), glycine (1.05 mg/mL) and polysorbate 80 (0.1 mg/mL), as summarized in Table 7.

TABLE 7

Components of the Formulation of PEG-Interferon Alpha Conjugate submitted to Lyophilization

| Components | Concentrations |
|---|---|
| $PEG_{12000}$-interferon alpha-2b | 0.178 mg/mL* |
| Sodium succinate, pH 6.8 | 10 mM |
| Lactose | 40 mg/mL |
| Trehalose | 16 mg/mL |
| Glycine | 1.05 mg/mL |
| Polysorbate 80 | 0.1 mg/mL |
| Purified water | 0.7 mL |

*Based on protein weight

Lyophilization was carried out by placing the above specified solution in glass containers followed by loading the glass containers in to a lyophilizer at ambient pressure and a temperature between 10° C. to 30° C. Samples were frozen gradually in controlled manner at ambient pressure and at a temperature between −40° C. to −55° C. over a period of 3 to 12 hrs. Subsequently, frozen samples were subjected to primary drying cycles at a temperature between −35° C. and −45° C. while maintaining a vacuum pressure from 500 mTorr to 50 mTorr. Following the primary drying cycles, secondary drying cycles were carried out for at least 6 hrs, under vacuum at a pressure between 20 to 30 mTorr. Upon completion of the lyophilization cycles, glass containers containing the lyophilized cakes were unloaded at ambient temperature and pressure.

After lyophilization, vials containing cakes with no defects were collected and stored at 5 (±3)° C., until used further for analysis. Samples were reconstituted with water for analysis at different periods of time, as specified in Table 8. The reconstituted solutions were checked for visual clarity. Stability of PEG-interferon alpha conjugate in lyophilization formulation was assessed by comparing the protein content, antiviral activity, and level of free interferon (degree of depegylation) present in the solution before and after lyophilization as shown in Table 8.

TABLE 8

Stability of Formulated PEG-Interferon Alpha Conjugate After Lyophilization

| Time (months) | Temp. (±3° C.) | Protein Content (µg/vial) | % Initial | Potency (IU/mg) | % Moisture | % Free IFN | Visual Clarity |
|---|---|---|---|---|---|---|---|
| Initial | 5 | 124.2 | 99.4 | $0.48 \times 10^8$ | 1.96 | 0.84 | CS |
| 3 | | nd | nd | $0.26 \times 10^8$ | 2.43 | 1.61 | CS |
| 6 | | nd | nd | $0.45 \times 10^8$ | nd | 1.87 | CS |
| 9 | | 122.2 | 97.8 | $0.85 \times 10^8$ | 2.33 | 2.20 | CS | nd—not determined;
CS—clear solution

Example 5

PEG-interferon alpha conjugate, at 0.2 mg/mL, was dissolved in an aqueous medium containing 10 mM sodium succinate buffer of pH 6.8, lactose (57.1 mg/mL), trehalose (22.8 mg/mL) and polysorbate 80 (0.1 mg/mL), and additionally with glycine (1.05 mg/mL) as summarized in Table 9.

TABLE 9

Components of the Formulation of PEG-Interferon Alpha Conjugate submitted to Lyophilization

| Components | Concentrations |
|---|---|
| $PEG_{12000}$-interferon alpha-2b | 0.143 mg/mL* |
| Sodium succinate, pH 6.8 | 10 mM |
| Lactose | 57.1 mg/mL |
| Trehalose | 22.8 mg/mL |
| Glycine | 1.05 mg/mL |
| Polysorbate 80 | 0.1 mg/mL |
| Purified water | 0.7 mL |

*Based on protein weight

Lyophilization was carried out by placing the above specified solution in glass containers followed by loading the glass containers in to a lyophilizer at ambient pressure and a temperature between 10° C. to 30° C. Samples were frozen gradually in controlled manner at ambient pressure and at a temperature between −40° C. to −55° C. over a period of 3 to 12 hrs. Subsequently, frozen samples were subjected to primary drying cycles at a temperature between −35° C. and −45° C. while maintaining a vacuum pressure from 500 mTorr to 50 mTorr. Following the primary drying cycles, secondary drying cycles were carried out for at least 6 hrs, under vacuum at a pressure between 20 to 30 mTorr. Upon completion of the lyophilization cycles, glass containers containing the lyophilized cakes were unloaded at ambient temperature and pressure.

After lyophilization, vials containing cakes with no defects were collected and stored at 5 (±3)° C., until used further for analysis. Samples were reconstituted with water for analysis at different periods of time, as specified in Table 10. The reconstituted solutions were checked for visual clarity. Stability of PEG-interferon alpha conjugate in lyophilization formulation was assessed by comparing the protein content, antiviral activity, and level of free interferon (degree of depegylation) present in the solution before and after lyophilization as shown in Table 10.

TABLE 10

Stability of Formulated PEG-Interferon Alpha Conjugate After Lyophilization

| Time (months) | Temp. (±3° C.) | Protein Content (µg/vial) | % Initial | Potency (IU/mg) | % Moisture | % Free IFN | Visual Clarity |
|---|---|---|---|---|---|---|---|
| Initial | 5 | 100.7 | 100.7 | $0.48 \times 10^8$ | 1.16 | 3.23 | CS |
| 3 |   | nd | nd | $0.24 \times 10^8$ | Nd | 2.28 | CS |
| 6 |   | 94.3 | 94.3 | $0.38 \times 10^8$ | Nd | 3.20 | CS | nd—not determined;
CS—clear solution

Free IFN content in all the examples above was determined by using HP-SEC analysis.

The Novel Lyophilized and Stabilized Formulations of Peg-Interferon Alpha Conjugates Described in the Present Invention have the Following Advantages.
1. Involve operational simplicity.
2. Involve use of cryoprotectants &/or lyoprotectants, which are less hygroscopic in nature.
3. Provide better physical strength to the lyophilized formulation.
4. All the above factors contribute to the cost effectiveness of the process of this invention.

We claimed:

1. A formulation comprising PEG-interferon alpha conjugates, a buffer, a stabilizer, a cryoprotectant and a solvent, wherein said buffer is selected from the group consisting of sodium phosphate, sodium succinate, potassium succinate, histidine chloride, sodium glycinate either alone or in combination, and said cryoprotectant is lactose.

2. The formulation as claimed in claim 1 wherein the stabilizer is selected from the group consisting of sodium dodecyl sulphate, and a polysorbate.

3. The formulation as claimed in claim 2 wherein the polysorbate is selected from the group consisting of Polysorbate 20, 40 and 80.

4. The formulation as claimed in claim 1 wherein the cryoprotectant further comprises trehalose.

5. The formulation as claimed in claim 1, wherein the concentration of the said PEG-interferon alpha conjugates is 0.03 to 2.0 mg interferon alpha per ml.

6. The formulation as claimed in claim 1, wherein the said buffer is sodium succinate.

7. The formulation as claimed in claim 6 wherein the concentration of sodium succinate buffer is in the range of 0.001 to 0.5 molar.

8. The formulation as claimed in claim 1, wherein the pH range of the said formulation is in the range of 4.0-6.8.

9. The formulation as claimed in claim 1, wherein the said stabilizer is present in a concentration of from 0.01 to 1.0 mg/ml.

10. The formulation as claimed in claim 1, wherein the concentration of cryoprotectant is between 10-100 mg/ml.

11. The formulation as claimed in claim 1, wherein said solvent is water.

12. The formulation as claimed in claim 1, wherein the composition further comprises glycine.

13. The formulation as claimed in claim 1, wherein said PEG-interferon alpha conjugates comprise predominantly single PEG molecules conjugated to single interferon alpha molecules.

14. The formulation as claimed in claim 1, wherein said interferon alpha molecules are selected from the group consisting of interferon alpha-2a, interferon alpha-2b, and interferon alpha-2c.

15. The formulation as claimed in claim 14, wherein said interferon alpha molecules are interferon alpha-2b.

16. A process of formulating a lyophilized powder, comprising:
providing a formulation comprising PEG-interferon alpha conjugates, a buffer, a stabilizer, lactose and a solvent, wherein said buffer is selected from the group consisting of sodium phosphate, sodium succinate, potassium succinate, histidine chloride, sodium glycinate either alone or in combination; and lyophilizing the formulation thereby producing the lyophilized powder.

17. A lyophilized formulation prepared according to the process of claim 16.

18. The formulation of claim 17 wherein the lyophilized powder is reconstituted with water.

19. The formulation as claimed in claim 1, wherein the concentration of the said PEG-interferon alpha conjugates is 0.03 to 2.0 mg interferon alpha per ml.

* * * * *